United States Patent [19]

Biemann et al.

[11] Patent Number: 4,843,243

[45] Date of Patent: Jun. 27, 1989

[54] METHOD AND APPARATUS FOR CONTINUOUS COLLECTION OF CHROMATOGRAPHIC EFFLUENT

[75] Inventors: Klaus Biemann, Alton Bay, N.H.; John J. Gagel, Cumberland Center, Me.

[73] Assignee: Massachusetts Institute of Technology, Cambridge, Mass.

[21] Appl. No.: 851,445

[22] Filed: Apr. 14, 1986

[51] Int. Cl.$^4$ ............................................. G01N 30/02
[52] U.S. Cl. ................................... 250/341; 250/288; 73/61.1 C; 422/70
[58] Field of Search ........... 250/341, 353, 328, 288 A; 356/36, 38, 244; 73/61.1 C; 210/657, 659; 422/66, 64, 70; 436/44, 46, 161

[56] References Cited

U.S. PATENT DOCUMENTS

| | | | |
|---|---|---|---|
| 3,570,555 | 3/1971 | Gilson | 422/64 |
| 3,704,955 | 12/1972 | Siegler, Jr. | 356/244 |
| 4,055,987 | 11/1977 | McFadden | 250/288 A |
| 4,267,451 | 5/1981 | Berick | 250/328 |
| 4,298,795 | 11/1981 | Takeuchi et al. | 250/288 A |
| 4,376,391 | 3/1983 | Brunnee | 250/288 A |
| 4,552,723 | 11/1985 | Adams et al. | 422/66 |

OTHER PUBLICATIONS

Castles et al., Paper delivered at the Pittsburgh Conference on Analytical Chemistry, 1984, Mar., Paper No. 655.
Azarraga et al., Paper delivered at the Pittsburgh Conference on Analytical Chemistry, 1984, Mar., Paper No. 656.
Fujimoto et al., "A New Sampling Technique for Reversed-Phase Liquid Chromatography/Fourier--Transform Infrared Spectrometry", *Analytica Chimica Acta.*, vol. 178, pp. 159-167 (1985).
S. Bourne et al., "Matrix Isolation GC/FTIR", 6 pages, *American Laboratory*, Jun. 1984.
Conroy et al., "Interface of a Microbore High-Performance Liquid Chromatograph with a Diffuse Reflectance Fourier Transform Infrared Spectrometer", pp. 822-825, *Analytical Chemistry*, vol. 57, No. 4, Apr. 1985.
Johnson et al., "Zero Dead Volume Flow Cell for Microbore Liquid Chromatography with Fourier Transform Infrared Spectrometric Detection", pp. 2642-2647, *Analytical Chemistry*, vol. 56, No. 14, Dec. 1984.
Sabo et al., "On-Line High-Performance Liquid Chromatography/Fourier Transform Infrared Spectrometry with Normal and Reverse Phases Using an Attenuated Total Reflectance Flow Cell", pp. 1822-1826, *Anal. Chem.*, vol. 57, No. 9, Aug. 1985.
Shafer et al., "Supercritical Fluid Chromatography/-Fourier Transform Infrared Spectrometry with an Automatic Diffuse Reflectance Interace", *Analytical Chemistry*, vol. 58, No. 1, pp. 58-64, Jan. 1986.
Kalasinsky et al, "Microbore High-Performance Liquid Chromatography/Fourier Transform Infrared Interface for Normal-or Reverse-Phase Liquid Chromatography", *Analytical Chemistry*, vol. 57, No. 9, pp. 1969-1974, Aug. 1985.
Johnson et al., "Reversed-Phase Liquid Chromatography with Fourier Transform Infrared Spectrometric Detection Using a Flow Cell Interface", *Analytical Chemistry*, vol. 57, No. 3, pp. 610-615, Mar. 1985.

(List continued on next page.)

Primary Examiner—Janice A. Howell
Assistant Examiner—William F. Rauchholz
Attorney, Agent, or Firm—Fish & Richardson

[57] ABSTRACT

Effluent from a liquid chromatograph is deposited onto a moving flat surface, which may be impervious to water, driven so as to define a continuous sample track in a generally circular, spiral or raster pattern. For infrared (IR) spectrographic analysis, the surface is IR reflective. In the preferred embodiment, effluent is deposited in a spiral pattern onto a rotating disc with a surface of reflective metal such as gold of aluminum. After collection, the reflection spectra can be interrogated by a Fourier transform IR spectroscopy. The same collection technique can be used to collect and mount samples for mass spectrometry.

36 Claims, 3 Drawing Sheets

OTHER PUBLICATIONS

Brown et al., "Speciation of Intermediate Polar Material in Coal Derived Process Solvents by Liquid Chromatography/Fourier Transform Infrared Spectrometry", *Analytical Chemistry*, vol. 55, No. 4, pp. 723–730, Apr. 1983.

Conroy et al., "Interface of a Reverse-Phase High-Performance Liquid CHromatograph with a Diffuse Reflectance Fourier Transform Infrared Spectrometer", *Analytical Chemistry*, vol. 56, No. 14, pp. 2636–2642, Dec. '84.

K. Jinno et al., "An Interface for the Combination of Micro High-Performance Liquid Chromatography and Infrared Spectrometry", *Applied Spoectroscopy*, vol. 36, No. 1, pp. 67–69, 1982.

Fujimoto et al, "Liquid Chromatography-Spectrometry with the Buffer-Memory Technique", *Journal of Chromatography*, 258 (1983), pp. 81–92.

Kuehl et al., "Novel Approaches to Interfacing a High Performance Liquid Chromatograph with a Fourier Transform Infrared Spectrometer", *Journal of Chromatographic Science*, vol. 17, pp. 471–476, Aug. 1979.

Brown et al., "Fourier Transform Infrared Spectrometric Detection in Size-Exclusion Chromatographic Separation of Polar Synfuel Material", *Analytical Chemistry*, vol. 53, No. 2, pp. 197–201, Feb. 1981.

METHOD AND APPARATUS FOR CONTINUOUS COLLECTION OF CHROMATOGRAPHIC EFFLUENT

The Government has rights in this invention pursuant to Grant Number 5-P01-ES01640-08 awarded by the National Institutes of Health.

BACKGROUND OF THE INVENTION

The invention relates generally to the field of chemical analysis concerned with identification of organic compounds in complex mixtures.

Liquid chromatography is a widely used separation process which relies on the differential adsorption properties of organic molecules. Typically an organic mixture in a specific solvent is added to the top of a tubular column which has been packed with a fixed bed of adsorbent material providing surface area onto which substances may be adsorbed. As the solvent and solute mixture descend through the column, more strongly adsorbed compounds coat the packed bed surfaces, referred to as the stationary phase. The less strongly adsorbed substances, proceed through the column, along with the solvent. Ideally, the substances are progressively retarded into well separated segments. The eluted separated components of the mixture are discharged from the other end of the column along with solvent or eluent. Properly separated, the organic compounds come out of the column at intervals spaced by relatively pure solvent effluent.

For high performance liquid chromatography (HPLC), narrow columns known as microbore columns, may be employed to reduce solvent consumption and promote high solute concentrations. A commercially available microbore HPLC column 50 cm long with a 1 mm internal diameter is loaded with 10 micrometer (um) silica beads. In normal phase chromatography, hydrocarbon solvents such as hexane and dichlormethane are used in the mobile phase. In reverse phase chromatography, polar organic solvents such as methanol are used in combination with water.

Once separated by chromatography, the individualized organic substances can be analyzed for identification by a variety of techniques, including, for example, infrared (IR) spectroscopy, mass spectrometry, nuclear magnetic resonance, differential refractometry, heat-of-absorption detection and modified hydrogen flame ionization detection. In particular, the high scan speed and sensitivity of Fourier transform infrared (FTIR) spectroscopy has greatly facilitated the recording of characteristic infrared spectra of the individual components of mixtures separated by chromatographic techniques. Organic molecules in general contain interatomic bonds which exhibit characteristic resonance frequencies, many of which happen to be in the mid-IR region. These can be identified in the absorption spectrum of the material by observing the portion of radiation not absorbed but transmitted or reflected from the substance. Indeed, FTIR spectroscopy has already proved highly successful for gas chromatography (GC) as opposed to liquid chromatography.

Gas chromatography is a process by which complex mixtures of chemical compounds are separated from one another by selective partition between a stationary liquid or solid phase and a mobil gas phase, typically employing hydrogen, helium, nitrogen or argon. Although simpler to interface with FTIR spectroscopy because these mobile phases do not absorb infrared radiation, gas chromatography is only useful for lighter more volatile compounds. Many high molecular weight compounds of interest in fossil fuel studies, for example, are beyond the range of gas chromatography because they are not sufficiently volatile for GC separation. Moreover, the sensitivity of the popular light pipe method of GC/FTIR is reduced for less volatile compounds due to high light pipe temperatures which reduces infrared transmission of the interface.

Interfacing HPLC with FTIR is hampered by infrared absorption of the extraneous solvent remaining in the mobile phase after separation. Two types of interfaces have appeared in the literature: (1) flow cells, which allow recording the IR spectra while the HPLC effluent flows by a window transparent in the infrared and (2) solvent deposition systems which involve transfer and elimination of the solvent on a medium compatible with infrared sampling.

In flow cells, the spectral contribution including spectral masking produced by the solvent material, which is still present at full strength, must be taken into account. Thus, analysis by the flow cell method is limited to solvents which happen to be transparent in wide regions of the infrared spectrum and even then, some areas of the spectrum will remain opaque resulting in loss of information and sensitivity.

Solvent deposition designs, on the other hand, have utilized diffuse reflectance (DR) FTIR and transmittance spectroscopy. The DR/FTIR interface involves the depositing of concentrated portions of HPLC effluent into a series of mesh-bottomed diffuse reflectance cups containing potassium bromide (KBr) powder, practically the only suitable material transparent over the entire intermediate infrared range examined in IR spectroscopy. Unfortunately, because KBr is water soluble, it is incompatible with reverse phase chromatography. In addition, the cups themselves and the manner of sequencing them under the discharge end of the column give rise to relatively complex mechanical designs. After the solvent (normal phase) has evaporated from a given cup, the cup is brought into the beam path of the spectrometer and the diffuse reflectance spectrum is recorded. Although this system has demonstrated good sensitivity, especially with microbore HPLC columns, it does not allow continuous analysis of the chromatographic effluent because the cups take discrete samples. This is a considerable disadvantage because a component can be missed or more than one component may collect in a single cup. Furthermore, continuous recording of the spectra offers advantages in the presentation and interpretation of the spectral data, such as Gram-Schmidt reconstructions, wavelength chromatograms or the plotting of successive spectra to identify closely eluting compounds.

Continuous collection with a DR/FTIR interface has been accomplished recently using super critical fluid (SCF) chromatography. The deposition of the sample onto a bed of KBr powder was facilitated by the easy elimination of the mobile phase ($CO_2$) which is a gas at atmospheric pressure. However, this particular principle does not appear to be applicable to conventional HPLC using liquid phases.

Transmission spectroscopy, as opposed to DR spectroscopy, is utilized in another solvent deposition system in which the effluent from a microbore HPLC flows directly onto a moving rectangular KBr crystal. After evaporation of the solvent, the crystal is passed through the spectrometer beam and transmission spectra are collected, thus providing a continuous spectral record of the chromatographic experiment.

In the past, the extension of either flow cell or solvent deposition interfaces to reverse phase chromatography employing aqueous solvents has required a solvent change before analysis. Unfortunately, the sensitivity of the technique is thereby reduced by at least an order of magnitude.

Laboratories involved in qualitative and quantitative analysis in chemical, biological, clinical and environmental research in general require more practical, reliable and versatile methods for analysis of compounds separated by HPLC.

SUMMARY OF THE INVENTION

Accordingly, the general objective of the invention is to provide an improved technique for collection of effluent of a liquid chromatograph, particularly an HPLC, compatible with aqueous as well as nonaqueous solvents and capable of continuous collection of effluent deposits. Another object of the invention is to perfect the HPLC/FTIR interface with a solvent deposition system allowing continuous collection of both nonaqueous and aqueous mobile phases yielding higher sensitivity at lower cost with greater versatility and simpler design. Still another object of the invention is to eliminate the problems associated with solvent absorbance in flow cell designs and reduce the complexity of previous solvent deposition designs while providing complete, continuous analysis on a surface impervious to aqueous solvents.

These and other objects of the invention are achieved in a solvent deposition system by deploying a moving plate having a preferably IR reflective front surface disposed beneath a discharge tube from a chromatograph column. A mechanical drive imparts substantially continuous relative motion between the effluent outlet and the plate parallel to the plane of the surface in order to define a continuous predetermined sample track on the surface of the plate. In this way, the effluent is continuously deposited upon the plate to form a relatively permanent record of separated components along a continuous sample track for subsequent analysis by IR spectroscopy, preferably reflectance-absorbance (R-A) FTIR spectroscopy. Following collection and solvent evaporation, the plate may be subjected to IR spectroscopy. The incident IR beam is directed to the area of interest along the sample track, preferably by a mechanical drive capable of the same motion used during collection. However, during spectroscopy the motion may be stopped, reversed and repeated at will to accommodate any scan program.

In the preferred embodiment, the plate is in the form of a flat circular disc having a planar reflective metal coating. The sample track is generally circular. A nonintersecting spiral is ideal for providing a long continuous track for efficient collection and IR spectroscopy. The effluent is preferably discharged through a nitrogen-powered nebulizer. In order to further hasten evaporation of the solvent, a nitrogen stream can impinge directly upon the recording surface.

In a preferred embodiment, IR spectroscopy is carried out with a fixed IR beam focused on an area lying on the simple track on the surface of the disc. The disc drive executes controlled circular or spiral motion causing the focused spot to precisely traverse the sample track. IR reflected from the sample track is collected preferably by a front surface concave mirror and redirected toward an open space on the reflective surface of the disc from which the beam is deflected to a stationary IR detector.

The system provides a practical and reliable method for infrared analysis of compounds and is compatible with all popular solvents and scan techniques for FTIR spectroscopy. High quality, compact discs can be mass produced at relatively low cost and are also reusable. The drive mechanism is inherently simple and can be programmed to tailor motions to specific applications.

The moving collection plate technique is compatible with mass spectrometry as well as other types of spectroscopy. In particular, the same plate used for continuous collection of effluent can be taken out of the collection system and placed in a mass spectrometer on a similar drive unit to present the sequential effluent deposits for ionization by an energy beam.

DETAILED DESCRIPTION

The embodiments described herein are specifically designed to facilitate reflectance-absorbance (R-A) FTIR spectroscopy of compounds deposited from a microbore HPLC. The system is applicable, however, to other species of spectroscopy as well as spectrometry and may be extended to nonmicrobore forms of liquid chromatography presenting a liquid effluent. In particular, the present system is of the solvent deposition type rather than the flow cell type. The system can also be extended from HPLC to handle super critical fluid chromatography without major design changes. Both SCF chromatography and HPLC are intended to be embraced by the term "liquid chromatography" as used herein.

Figure 1:
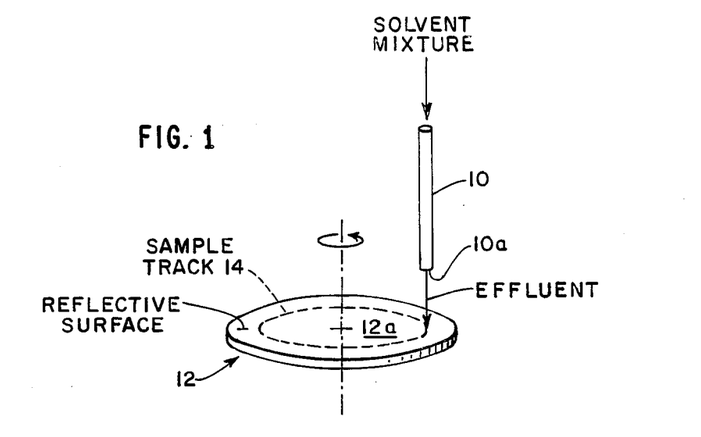
FIG. 1 is a perspective schematic representation of the continuous chromatographic effluent collection system according to the invention.
Figure 2:
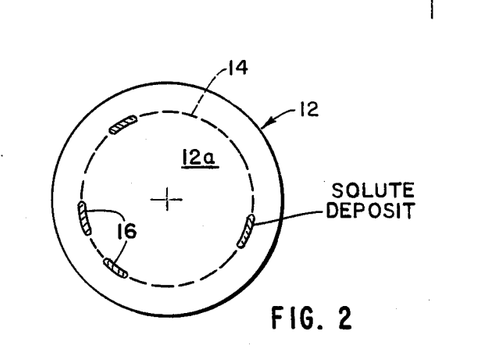
FIG. 2 is a plan view of the disc surface with a circular sample track.

As shown in FIG. 1, effluent from a microbore HPLC column 10 having a discharge end 10a is deposited onto a circular disc 12 having a highly IR reflective front surface 12a of material, such as aluminum or preferably gold, which is impervious to nonaqueous and aqueous solvents. The disc is arranged so that the reflective surface 12a is substantially horizontal to discourage running of the effluent deposit. The disc 12 is rotated about its axis as shown to define a circular sample track 14 for the effluent. As shown in FIG. 2, as the disc 12 rotates, effluent including any remaining solvent is deposited along the track 14. After the solvent evaporates, only the solute deposits 16 remain. If the solute has been properly separated, a series of spaced deposits are collected, as shown in FIG. 2. With a constant average rotation speed, the intervals between the solute deposits 16 correspond to the amount by which each successive component was chromatographically retarded. The metal surface 12a of the disc 12 allows for continuous collection of chromatographic effluent without limitation to particular solvents because the deposition surface 12a is inert to all common HPLC solvents.

Figure 3:
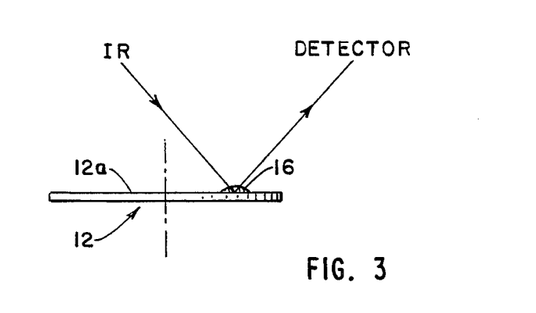
FIG. 3 is a schematic side representation of the disc undergoing IR spectroscopy.

After collection, the disc 12 is removed from the chromatographic apparatus and subjected to IR spectroscopy by training an IR beam on the solute deposits 16 along the sample track 14. The impinging IR beam is partially reflected after passing through the deposit 16 toward an IR detection system. The disc shaped mirror 12 may be rotated by a drive unit while spectra are recorded continuously. Alternatively, the disc can be rotated to a particular solute deposit and then stopped or reversed for repeated analysis of specific deposits.

Figure 4:
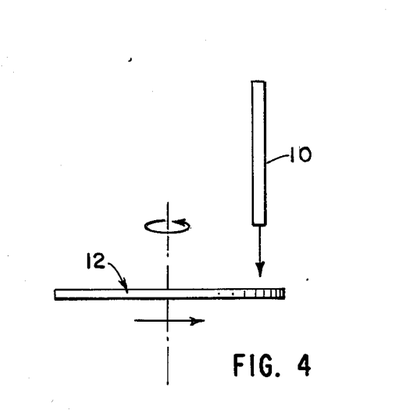
FIG. 4 is a schematic representation of the disc collection system of FIG. 1 with the drive mechanism modified to achieve a spiral track.
Figure 5:
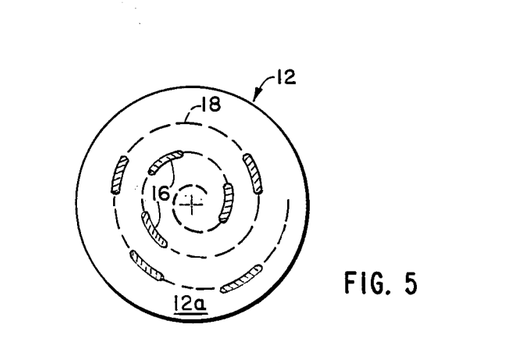
FIG. 5 is a plan view of the disc of FIG. 4 illustrating the spiral sample track.

As shown in FIGS. 4 and 5, the axis of rotation of the disc can be translated continuously or stepwise toward the effluent to achieve a long, continuous spiral sample track 18 as shown in FIG. 5. The spiral pattern expands the amount of chromatographic data obtainable with a single disc and thus may reduce its size.

Figure 6:
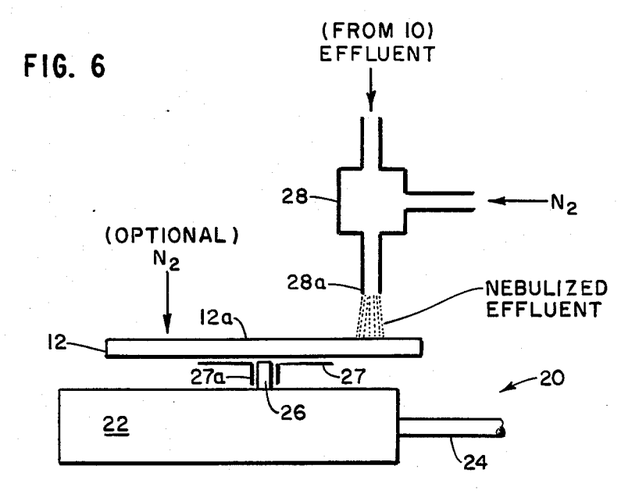
FIG. 6 is a schematic representation showing the disc viewed from the side in a preferred embodiment.

Experimental apparatus implementing the design of FIG. 1 is shown in FIG. 6. The disc 12 is mounted for rotation by a drive unit 20 including gear box 22 driven by a stepper motor through drive shaft 24. While a stepper motor does move stepwise or incrementally, the motion is referred to herein as substantially continuous for a series of rapid consecutive steps. Drive shaft 24 may be a removable or flexible shaft for ease of assembly and operation. The gear box 22 is machined from a block of aluminum and bored to provide space for right angle gears (not shown) to meet approximately 4 cm from its base. A vertical output shaft 26 extends above the gear box 22. The mirror attachment assembly is an aluminum disc 27 with three raised pods (not shown) on one side to which the underneath face of the disc 12 is epoxied. The attachment assembly 27 has a drilled central protrusion 27a which fits over the vertical shaft 26 on the gear box. The protrusion 27a has a tapped hole perpendicular to the shaft 26 which allows the assembly to be secured to the shaft by means of a set screw (not shown). With a stepper motor capable of 2,000 steps per revolution, for a typical sample track with a radius of 2.5 cm, each step corresponds to 0.08 mm.

HPLC effluent is brought to a mixing Tee 28 from a conventional UV detector by a short length of stainless steel tubing (not shown). The outlet of the Tee is fastened to a syringe tip 28a. Fitting the syringe tip to the Tee port is accomplished by forcing Teflon tubing over the tip to give the proper external diameter and to make a gas tight liquid tight seal. The tip of the syringe is preferably held about 3 mm above the mirror surface 12a and results in a 1 to 2 mm wide solute deposit track. The other inlet to Tee 28 is connected to a source of pressurized nitrogen gas to nebulize the effluent. Nebulized effluent comes out of the syringe tip 28a just above the surface 12a of the collection disc 12. The nebulizer helps the solute dry faster and reduces residue on the syringe tip 28a. A gentle stream of nitrogen may be passed over the nebulized solvent after contacting the mirror surface 12a to rapidly evaporate any remaining solvents.

The discharge rate from a microbore column is typically 30 microliters per minute and chromatographic peaks are about 1 minute wide. Thus, rotational speeds of 4 mm/min measured along the sample track are used to provide a deposit length comparable to the beam width of the FTIR spectrometer.

Figure 7:
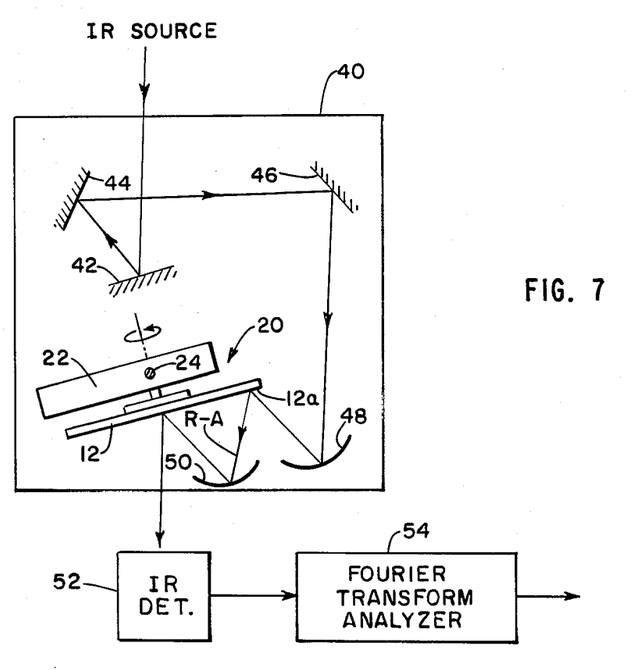
FIG. 7 is a plan schematic representation and block diagram illustrating the FTIR spectrographic apparatus with a reflectance accessory modified according to the invention.

After collection and evaporation of the solvent, the disc 12 is removed to a reflectance accessory 40 shown in FIG. 7 in a FTIR spectrometer, for example, a Digilab Model 15/90E. A prototype reflectance accessory was constructed from a Barnes Analytical Model 126 Reflectance Accessory modified by removal of the sample holder and a final plane mirror which directed the beam toward the detector. The drive unit 20 and mirror disc 12 are designed to take the place of these components. That is, the same mechanical apparatus shown in FIG. 6 (without the Tee, of course) is relocated following collection to the reflectance accessory 40.

A series of fixed plane mirrors 42, 44 and 46 directs the modulated infrared beam of a Fourier transform IR spectrometer. A concave focusing mirror 48 focuses the IR beam onto the sample track on the surface of the disc 12 for analysis of deposits. The R-A radiation reflected from the sample track is collected by concave front surface mirror 50 and redirected toward the center of the circular mirror 12 which reflects it onto an IR detector 52 whose output is fed to a Fourier Transform analyzer 54. In the Digilab Model 15/90E the detector 52 is a liquid-nitrogen-cooled wide band mercury/cadmium/telluride detector coupled with an interferometer operating at a moving mirror speed of 1.2 cm per second.

The 3-power beam condensing optics in the Barnes reflectance accessory aimed at a 20 degree incident angle to the disc 12 provided about a 2 mm spot size on the surface 12a with the spectrometer source aperture set to 6 mm. Under these conditions, the throughput of the reflectance unit with the device installed was just below the maximum dynamic range of the 15 bit analog-to-digital converter in the analyzer 54.

In operation, utilizing the circular track system of FIG. 1 and 2, effluent is collected at about 5 mm from the edge of the rotating mirror at a deposition speed of about 4 mm per minute. Under these conditions, a forty minute chromatographic run can be collected in a single track. FTIR spectroscopy allows continuously collected data to be obtained with software intended for GC/FTIR set to coadd eight scans at 8 cm$^{-1}$ resolution before transforming to form a scan set. This system provides a time resolution of 1.4 seconds. Gram-Schmidt chromatograms were calculated using reference vectors from a blank spot on the reflective surface or by reconstructing the data from interferograms taken during the run. The selection of coaddition regions for spectra of components from chromatographic runs was accomplished by using the automatic peak finding software available with the GC/FTIR software package. Wavelength chromatograms were created by Digilab supplied software which monitors absorbance at a user specified frequency throughout the chromatographic run or any portion thereof. For R-A spectra which shows excessive base line sloping or curvature due to scattering from the sample, a piecewise linear tracing of the base line can be generated using Digilab software. Subtraction from the raw spectrum provides a flatter base line and facilitates peak intensity comparison with standard spectra obtained using KBr powder. Sensitivity of the method according to the invention is increased by depositing the material over the smallest possible surface area and focusing the beam to a corresponding spot.

The ability to analyze the chromatographic run in a continuous fashion allows the use of the Gram-Schmidt reconstruction technique to indicate the presence of a deposited component and also the use of wavelength of chromatograms to further interrogate the data for the presence of certain characteristic absorbance bands.

An important advantage of FTIR over conventional grating instruments is the ability to enhance spectral data by signal averaging many scans. The design of the preferred embodiment provides a record of the chromatographic separation which may be analyzed noncontinuously and may thus take advantage of these signal averaging capabilities. For continuous collection, lower resolution spectra are collected to increase time resolution and to save computer storage space. For noncontinuous analysis of selected components, there are no such concerns. The enhancement of minor separated components also can be accomplished in this way.

The design has other inherent advantages. During the collection step, the mirror speed may be reduced to enhance sensitivity by concentrating more material in a smaller track area or enhance the infrared chromatographic resolution by using a faster speed. With a computer controlled motor drive, the rotation of the mirror can be programmed to vary the speed during the chromatographic run to optimize resolution and sensitivity.

Although the present device could be developed for use on-line with the deposition step carried on inside the spectrometer, this would necessitate extracting solvent vapors which can interfere with the adsorption spectra. The time saved in the on-line experiment is small compared to the time required for sample preparations and analysis of the infrared data.

Figure 8:
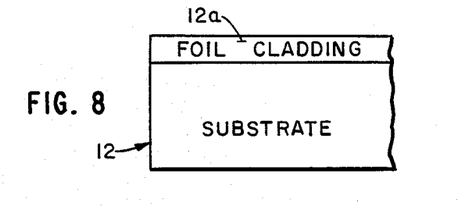
FIG. 8 is a sectional schematic view of the disc of FIG. 1 in the form of a foil clad substrate.
Figure 9:
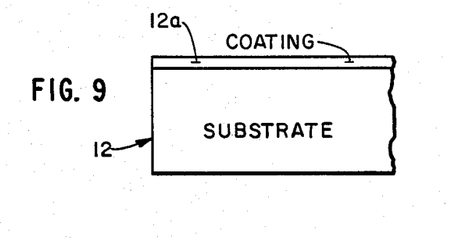
FIG. 9 is a sectional schematic representation of another embodiment of the disc of FIG. 1 in the form of a substrate with a deposited or plated coating.
Figure 10:
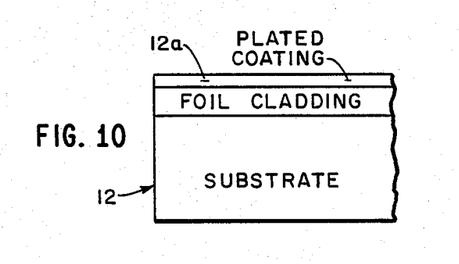
FIG. 10 is a sectional schematic representation of another embodiment of the disc of FIG. 1 in the form of a foil clad substrate with a plated coating over the foil.

FIGS. 8, 9 and 10 illustrate three different techniques for preparing the disc 12. Foil cladding, deposited or plated coating or a combination of both, in which a plated coating is formed over the foil cladding, are all possible techniques. A smooth, flat reflective surface is important. An aluminum layer deposited on glass, as in FIG. 9, has been found to be suitable. Even better results can be expected from gold plated over copper or deposited on a glass substrate.

Figure 11:
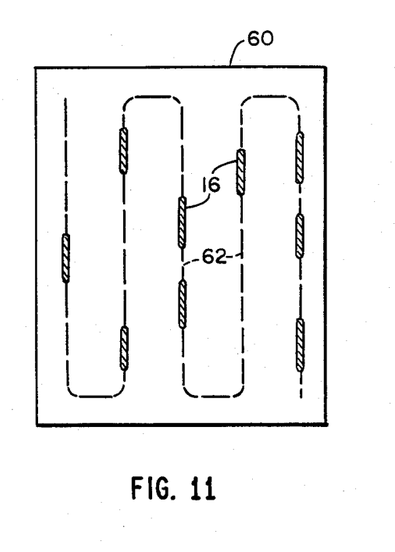
FIG. 11 is a plan schematic representation of another embodiment of the collection plate in rectangular form with a sample track in a raster pattern.

FIG. 11 shows another embodiment of the collection plate which instead of being in the form of a disc 12 is in the form of a rectangular plate 60. In this design, the drive unit (not shown) is modified to execute a raster scan pattern for the sample track 62. Solute deposits 16 are left on the surface 60a along the raster track.

Figure 12:
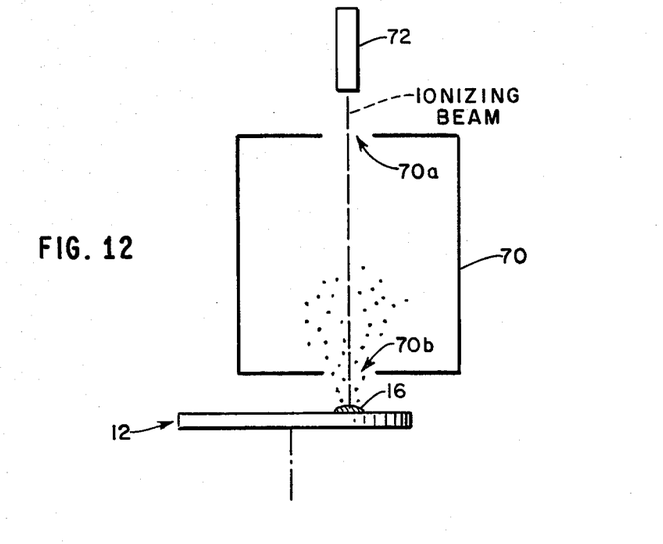
FIG. 12 is a schematic representation illustrating a chromatographic collection disc undergoing mass spectrometry according to the invention.

Mass spectrometry provides another possible means of identification of components separated by liquid chromatography. The collection system of the present invention is not only compatible with but also advantageous for all forms of mass spectrometry, including Fourier transform, magnetic deflection, time-of-flight and quadrapole spectrometry. A Fourier transform mass spectrometer is diagrammed in FIG. 12. An ionizing cell 70 having means for producing electrical and magnetic fields (not shown) has aligned ports 70a and 70b to allow a beam of ionizing radiation to pass through the cell to the sample located beneath port 70b. The sample to be ionized is carried on the collection disc 12 or rectangular plate 60 (FIG. 11) on which deposits 16 have been continuously collected during chromatography. The disc 12 and ionizing trapping cell 70 are in a vacuum chamber (not shown). A beam of ionizing radiation, for example, from a high power laser 72, impinges on the deposit 16 generating ions of the sample material which are drawn through the opening 70b into the trapping cell 70. For mass spectrometry, an IR reflective surface on the disc 12 is unnecessary although acceptable. Indeed, following chromatographic collection, the same disc 12 could be subjected sequentially to IR spectroscopy and then mass spectrometry to obtain comparative spectra for verification or further analysis.

For time-of-flight mass spectrometry with $252_{Cf}$ desorption, the samples are preferably carried on a thin foil surface. The foil-clad disc construction illustrated in FIG. 8 can be used in collection and spectrometry.

The reflective continuous collection plate technique represents a novel approach which eliminates the problems associated with solvent absorbance in flow cell designs and reduces the inherent complexity of previous solvent deposition techniques while providing complete continuous collection and analysis on a surface impervious to aqueous as well as nonaqueous solvents. The system used in HPLC is capable of sensitivity in the nanogram range. The sample plates are compact, inexpensive to manufacture and reusable. Depending on the length of the continuous track and angular velocity of the disc, several runs can be recorded on the same disc. The discs are compatible with all types of spectroscopy and mass spectrometry. Rotational speed can be programmed to tailor the deposition area or to maximize resolution of closely eluting compounds. The design of the system allows many scans of many samples to be easily taken and stored for computation. A variety of scan programs can be accommodated—from a continuous survey scan along the entire track to detailed examination of a single deposit. Using averaging techniques makes the spectroscopy results more reliable. The intervals between deposits can be examined as a time record of separation intervals. Identification markings can be easily added to the discs to catalog the relatively permanent physical record in which the order of components for each entire chromatographic run is preserved. A portable drive unit system allows the same mechanism to be employed for collection and spectroscopy at different locations insuring that the sample track is followed accurately during off-line spectroscopy or mass spectrometry.

The foregoing description is intended to be only illustrative of several forms in which the invention may be implemented. Any number of variations and modifications are possible without departing from the principle of the invention. For example, the HPLC system can be modified to accommodate super critical fluid chromatography. Other shapes of the collection plate or sample track are possible besides those shown herein and other means of imparting relative motion between the nebulizer and the reflective surface are, of course, possible without affecting the principle of operation. The scope of the invention is indicated, of course, by the appended claims and equivalents thereto.

What is claimed is:

1. Apparatus for continuous collection and off-line recording of components separated by chromatography, comprising
   means for discharging effluent with solute and mobile phase from a chromatograph,
   means for eliminating substantially all of the mobile phase from the discharged effluent;
   a removable compact rigid unitary plate having a planar IR reflective surface,
   support means for removably mounting said plate so that said surface is horizontally disposed to receive said solute, and
   mechanical drive means for imparting relative motion between said discharge means and said plate to define a continuous predetermined sample track on the surface of said plate,
   such that the solute substantially without the mobile phase is deposited on the plate to form a record of separated components along said continuous sample track for subsequent analysis by IR spectroscopy.

2. The apparatus of claim 1, wherein said reflective surface is impervious to water.

3. The apparatus of claim 1, wherein said sample track is nonintersecting.

4. The apparatus of claim 1, wherein said plate is in the shape of a disc.

5. The apparatus of claim 1, wherein said relative motion is generally circular.

6. The apparatus of claim 1, wherein said sample track is spiral.

7. The apparatus of claim 1, wherein said plate includes an IR reflective coating on a substrate.

8. The apparatus of claim 1, further comprising an IR spectroscopy system independent in time and location with respect to said collection and recording apparatus, including
   means disconnected from said collection and recording apparatus for receiving and supporting said plate in a predetermined position,
   means for directing an IR beam toward an area of incidence on said predetermined sample track,
   means for imparting relative motion between said beam and said plate so that the area of incidence of said beam is movable along said predetermined sample track,
   radiation collection means for receiving IR radiation reflected from said area of incidence for producing an output,
   detector means receiving the output of said radiation collection means for detecting the varying level of IR reflection along said sample track and for producing an output indicative thereof, and
   analyzer means responsive to the output of said detector means for producing an output indicative of the IR spectra along said sample track.

9. The apparatus of claim 8, wherein said radiation collection means includes a concave mirror which redirects IR radiation toward a portion of said reflective surface away from said sample track so that it is reflected therefrom toward said detector means.

10. The apparatus of claim 8, wherein both said means for imparting relative motion are substantially identical.

11. The apparatus of claim 10, wherein both said support means and means in said collection and recording apparatus for imparting relative motion are removable and portable, further comprising
    means in said spectroscopy system for receiving said portable support means and motion imparting means.

12. Apparatus for analyzing IR spectra of components separated independently in time and location by chromatography, comprising
    means for receiving a unitary rigid sample plate having a planar fully IR reflective surface,
    means for directing an IR beam toward said surface,
    mechanical drive means for imparting relative motion between the area of incidence of said beam and said plate so that said area of incidence is movable along a predetermined continuous sample track predefined on said surface,
    collection means arranged to continuously receive IR radiation reflected from said area of incidence along said sample track for producing an output,
    detector means for receiving the output of said collection means and producing an output indicative of the level of IR reflection along said sample track, and
    analyzer means responsive to the output of said detector means for producing an output indicative of the IR spectra along said sample track.

13. The apparatus of claim 12, wherein said collection means includes a curved mirror which deflects collected IR radiation toward a predetermined area on said reflective surface away from said sample track so that it is reflected therefrom toward said detector means.

14. The apparatus of claim 12, wherein said means for imparting motion includes turntable means for rotating said plate about a rotational axis normal to the plane of said surface.

15. The apparatus of claim 14, wherein said means for imparting motion further includes translating means for imparting linear motion along a line generally between said area of incidence and the rotational axis of said plate to define a spiral sample track.

16. A method of preparing off-line a sample for spectroscopy or spectrometry by continuous collection of components separated by chromatography, comprising the steps of
    discharging chromatographic effluent including mobile phase and solute,
    substantially eliminating the mobile phase from the discharged effluent, and
    depositing chromatographic effluent substantially without the mobile phase along a continuous predetermined sample track on a removable compact rigid unitary planar fully IR reflective surface, said surface being constructed such that it may be readily removed from the chromatographic device and subsequently readily received by a spectrometer or spectroscopy device.

17. The method of claim 16, wherein said surface is impervious to water.

18. The method of claim 16, wherein said sample track is generally circular.

19. The method of claim 16, wherein said sample track is in the shape of a planar spiral.

20. The method of claim 16, wherein said step of depositing includes rotating said surface about an axis normal thereto.

21. The method of claim 20, wherein said step of rotating includes rotating at a substantially continuous speed.

22. The method of claim 20, wherein said step of depositing further includes translating said axis of rotation to define a spiral sample track.

23. The method of claim 20, wherein said step of rotating includes rotating at a discontinuous speed to optimize the deposition area.

24. The method of claim 16, further comprising the step of
preparing said reflective surface by applying a reflective coating to a nonmetallic substrate.

25. A method of preparing and analyzing continuously collected components separated by chromatography, comprising the steps of
depositing chromatographic effluent along a continuous predetermined sample track on a removable compact rigid unitary planar fully IR reflective surface, and
after collection and evaporation of the solvent, relocating said reflective surface in its entirety and directing an infrared beam, independently in time and location with respect to said depositing step, toward deposits along said sample track on said surface in accordance with a predetermined scan program for IR spectrogrpahic analysis.

26. The method of claim 25, wherein said step of depositing includes rotating said surface about an axis normal thereto.

27. The method of claim 26, wherein said step of depositing further includes translating said rotational axis to define a spiral sample track.

28. The method of claim 25, wherein said steps of depositing and directing said infrared beam are carried out by imparting corresponding motion to said surface about a normal axis therethrough.

29. The method of claim 28, wherein said steps of depositing and directing said beam further comprise imparting corresponding motion to said surface by translating said axis.

30. The method of claim 25, further comprising the step of
forming said reflective surface by applying an IR reflective coating to a substrate.

31. The method of claim 25, further comprising the step of
forming said reflective surface by laminating a reflective foil to a substrate.

32. The method of claim 25, wherein the step of depositing is carried out by imparting substantially continuous motion to said surface along said sample track and
the step of directing said infrared beam along said sample track is carried out by imparting substantially discontinuous motion to said surface.

33. A method of preparing and presenting a series of samples for mass spectrometry, the mass spectrometer separated independently in time and location from a chromatographic device comprising the steps of
depositing chromatographic effluent along a continuous predetermined sample track on a removable planar collection surface,
following collection and evaporation of solvent, relocating said surface in its entirety to a mass spectrometer, and
moving said surface to bring each successive deposit into alignment with an ionizing beam of said mass spectrometer.

34. The method of claim 33, further comprising the step of
preparing said collection surface by laminating a metal foil to a substrate.

35. The method of claim 33, wherein said depositing step is accomplished by continuously moving said surface while collecting effluent deposits and the subsequent step of moving said surface to bring deposits into alignment with the ionizing beam of a mass spectrometer is accomplished by continuously moving said surface.

36. The method of claim 33, wherein said depositing step is accomplished by continuously moving said surface while collecting effluent deposits and the subsequent step of moving said surface to bring deposits into alignment with the ionizing beam of a mass spectrometer is accomplished by discontinuously moving said relocated surface.

* * * * *

UNITED STATES PATENT AND TRADEMARK OFFICE
CERTIFICATE OF CORRECTION

PATENT NO. :  4,843,243
DATED      :  June 27, 1989
INVENTOR(S):  Klaus Biemann and John J. Gagel It is certified that error appears in the above-identified patent and that said Letters Patent is hereby corrected as shown below:

Column 1, line 66, "mobil" should be --mobile--.

Column 10, line 12, insert --removable compact-- before "unitary".

Column 12, line 16, insert --,-- after "device".

Signed and Sealed this

Third Day of July, 1990

*Attest:*

HARRY F. MANBECK, JR.

*Attesting Officer*      *Commissioner of Patents and Trademarks*